United States Patent [19]

Nadal

[11] Patent Number: 5,725,550
[45] Date of Patent: Mar. 10, 1998

[54] FILTRATION UNIT FOR RETAINING BLOOD CLOTS

[75] Inventor: Guy Nadal, Poitiers, France

[73] Assignee: B. Braun Celsa (Societe Anonyme), Chasseneuil Du Poitou, France

[21] Appl. No.: 689,623

[22] Filed: Aug. 9, 1996

[30] Foreign Application Priority Data

Aug. 10, 1995 [FR] France .................... 95 09737

[51] Int. Cl.⁶ .............................. A61F 2/02; A61B 17/00
[52] U.S. Cl. ............................. 606/200; 606/198
[58] Field of Search ................... 606/200, 108, 606/194, 195, 198; 623/1; 604/104, 106

[56] References Cited

U.S. PATENT DOCUMENTS

| | | | |
|---|---|---|---|
| 4,817,600 | 4/1989 | Herms et al. ............... | 606/200 X |
| 4,832,055 | 5/1989 | Palestrant . | |
| 5,059,205 | 10/1991 | El-Nounou et al. .......... | 606/200 |
| 5,133,733 | 7/1992 | Rasmussen et al. .......... | 606/200 |
| 5,300,086 | 4/1994 | Gory et al. .................. | 606/200 |
| 5,324,304 | 6/1994 | Rasmussen .................. | 606/200 |
| 5,344,427 | 9/1994 | Cottenceau et al. .......... | 606/200 |
| 5,383,887 | 1/1995 | Nadal ......................... | 606/200 |

FOREIGN PATENT DOCUMENTS 2666980    3/1992    France .

*Primary Examiner*—Michael Buiz
*Assistant Examiner*—Nancy Mulcare
*Attorney, Agent, or Firm*—Rothwell, Figg, Ernst & Kurz, PC

[57] ABSTRACT

The invention relates to a blood filtration unit which is to be implanted in a vessel (11) of a patient's body, especially for retaining blood clots, comprising a first filter (2) which is to be implanted temporarily, a first catheter (20) for introducing the first filter (2) into the vessel, a second filter (1) which is to be implanted permanently, the second filter (1) having a central opening of which the diameter is sufficiently large to permit the passage of the first filter (2) through it, and a second catheter (22) for introducing the second filter (1) into the vessel (11) and for removing the first filter (2) from the vessel (11).

7 Claims, 3 Drawing Sheets

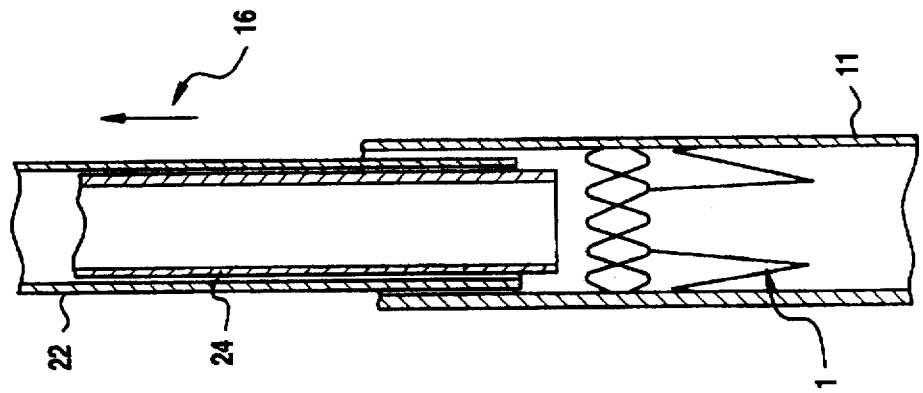
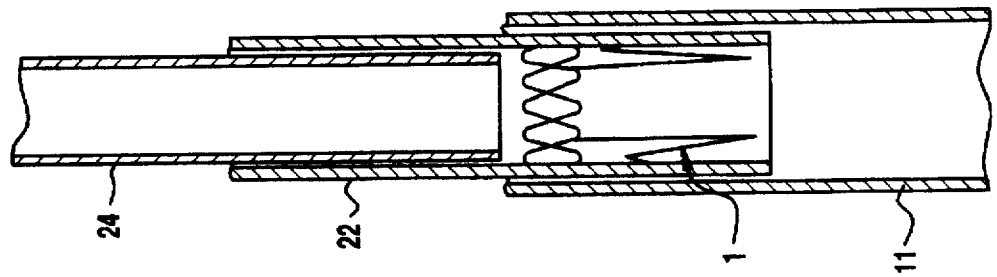
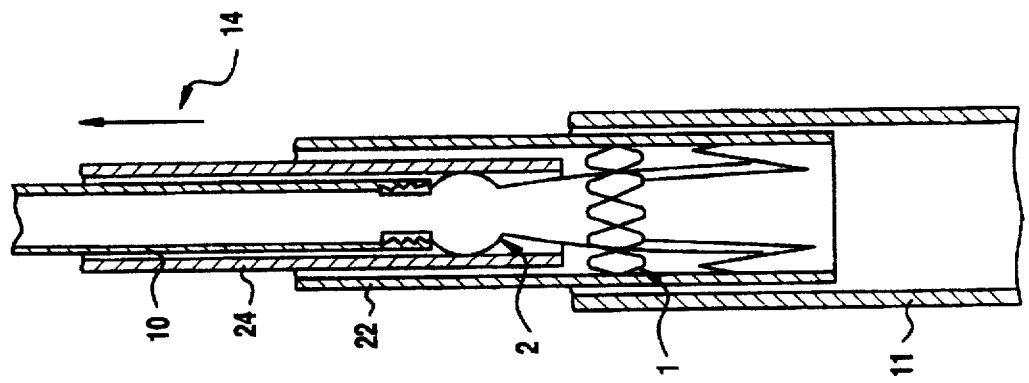

FILTRATION UNIT FOR RETAINING BLOOD CLOTS

The invention relates to a blood filtration unit which is to be implanted inside a vessel of a patient's body.

Currently known filtration units are formed by at least one filter which is implanted intravenously, generally into the inferior vena cava, to stop blood clots which could migrate towards the heart, in order to avoid the risk of embolism.

The blood filters used may be classified essentially in two categories.

The first category is that of filters that are to be implanted permanently in patients where the risk of embolism is chronic. Some conventional permanent filters have, for example, a frustoconical structure comprising a series of branches terminated by hooks which enable the filter to be secured permanently to the vessel wall.

The second category is that of filters that are to be implanted temporarily in patients where the risk of blood clot migration lasts only for a brief period, usually a few weeks. Temporary filters differ from permanent filters basically in that they do not comprise hooks for securing to the vessel. The branches simply rest on the vessel wall without hooking into it. These filters are also connected throughout the entire period of implantation to a support rod, the essential role of which is to prevent them migrating into the vessel and which enables them to be withdrawn from the vessel at the end of the implantation period.

In some patients, it also happens that the risk of embolism remains great and is prolonged over time contrary to what was expected. If a temporary filter has been implanted first, it is then generally necessary to remove it in order to replace it by a permanent filter.

For that purpose, document FR A-2 666 980 proposes a filtration unit enabling a permanent filter to be implanted through a temporary filter still in place in the vessel, and the temporary filter can be removed or can remain where it is after the permanent filter has been implanted.

A filtration unit of that type is very advantageous for the patient because its use requires only a small number of surgical interventions and thus reduces risks.

However, in spite of its great value, it seems that in practice this unit has some disadvantages which are due in particular to the structure of the various filters of which it is composed.

Owing to the fact that the temporary filter has to permit the permanent filter to pass through it, its dimensions are relatively large and may be troublesome to the patient.

On the other hand, the permanent filter has to be sufficiently small first to be introduced, while already contained in an introducing sleeve, into the support rod connected to the temporary filter and then to pass through the temporary filter. It will be appreciated that, in order to observe these size requirements, it is necessary to use permanent filters of reduced performance.

The invention therefore proposes a solution which enables the advantages of such a blood filtration unit to be preserved while at the same time providing for the use of filters having both excellent filtration qualities and dimensions such that they do not trouble the patient.

To that end, the blood filtration unit according to the invention is characterised in that it comprises:

a first blood filter adapted to be temporarily implanted in the vessel, during a first period of time, said first blood filter comprising:

a filtration structure having an axis and being adapted for having a first reduced diameter in a first radially folded state, for the implantation thereof, and a second enlarged diameter greater than the first diameter, in a radially expanded state, upon implantation of said filtration structure in the vessel, an elongated flexible support-stem having an end fixed to said filtration structure, the elongated support stem having a length enough for controlling a movement of the filtration structure, from outside the patient body, a first catheter adapted to be introduced into the vessel and adapted for containing the first blood filter in its first radially folded state, fot the implantation thereof in the vessel, a second blood filter adapted to be permanently implanted in the vessel, during a second period of time following the first period of time, the second blood filter having a central hole for allowing the passage therethrough of the first blood filter in its first radially folded state, the second blood filter being adapted for having a first reduced diameter in a first radially folded state, for the implantation thereof in the vessel, and a second enlarged diameter greater than the first diameter, in a second radially expanded state, upon implantation of said second blood filter in the vessel, a second catheter adapted to be introduced in the vessel and adapted for containing the second blood filter in its first radially folded state, for the implantation thereof in the vessel, and/or for containing the first blood filter in its first radially folded state for removing thereof out of the vessel, at the end of said first period of time.

The various features and advantages of the invention will emerge even more clearly from the following description which is given with reference to the appended drawings, in which:

FIGS. 4 to 10 show various successive stages of the implantation of the blood filtration unit according to the invention.

FIG. 1 shows a filter generally indicated 2 which is included in the filtration unit according to the invention and which is to be implanted in a vessel for a temporary period. This filter will be referred to as the "temporary filter" in the following description.

Figure 1:
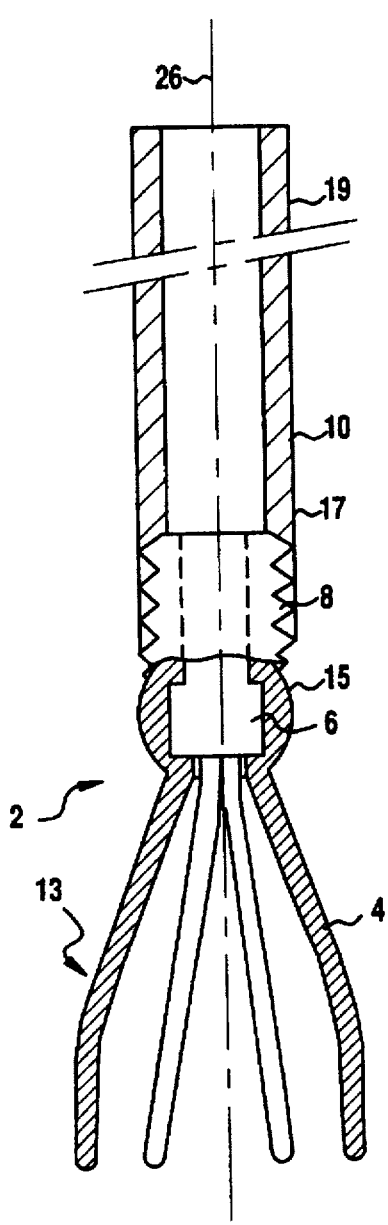
FIG. 1 is a diagram of the first filter which is included in the unit according to the invention and which is to be implanted temporarily.

This filter may be a known temporary filter, for example such as described in the above-mentioned application FR A-2 666 980. However, although it has the same structure, the filter used in the unit according to the invention is smaller.

The filter comprises a resilient structure having a distal end 13 (corresponding to the end furthest away from the place of introduction when the filter is in place in the vessel) formed by several legs 4, which are connected to one another in the area of the proximal end 15 (the end nearest the place of introduction) of the filter, and comprising an extension 8 connected to the distal end 17 of a support rod 10. The legs 4 may especially be in the form of fine strips or fine threads of metal produced from special steel of the cobalt-chromium type, such as "phynox" (registered trade mark).

The support rod 10 preferably has a length at least equal to the distance separating the place of introduction from the place of implantation. Thus, it is easy to remove the filter 2 at the end of its period of implantation, simply by pulling the support rod 10.

In order to enable the filter 2 to be introduced into the vessel 11, its distal end can adopt a first state in which it has a substantially tubular rectilinear shape. Once the filter is in place in the vessel, its distal end expands into a substantially conical shape.

The temporary filter 2 shown diagrammatically also comprises a central opening 6 of small diameter and axis 26 enabling it to slide along a guide wire.

Figure 2:
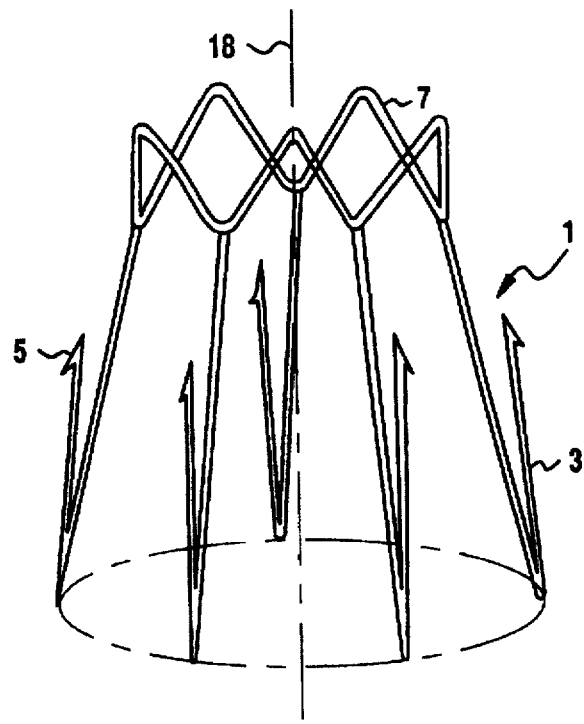
FIGS. 2 and 3 are diagrams of two particular embodiments of a second filter which is included in the unit according to the invention and which is to be implanted permanently in a vessel.

Referring to FIG. 2, it will be noted that the filter, which is generally indicated 1 and which will be referred to more simply as the "permanent filter" in the following description, comprises a series of elongated branches or legs 3 each of which is substantially "V"-shaped. One of the free ends of each "V" comprises fixation means such as a hook 5 for anchoring the filter to the vessel wall. The other end is connected to a metal thread, for example produced from "phynox" (registered trade mark) which has a succession of corrugations or ondulations (such as zig-zags) forming a resilient annular structure 7 of which the central opening has a diameter which can be more or less "constricted" and which is adapted to permit the passage of the temporary filter. The various branches 3 can be produced in the form of fine metal threads of "phynox" (registered trade mark) and are secured around the annular structure or ring 7 However, the whole of the filter could also be produced in a single metal piece, its structure being obtained by cutting.

In order to be introduced into the vessel, the permanent filter 1 can adopt a constrained state in which the elongated branches or legs 3 are moved close up to the axis 18 of the central opening of the filter until they are substantially parallel thereto. When it is in place in the vessel, the filter adopts a radially expanded state, the branches 3 then moving away from the axis 18 and the hooks 5 anchoring themselves in the vessel wall.

Figure 3:
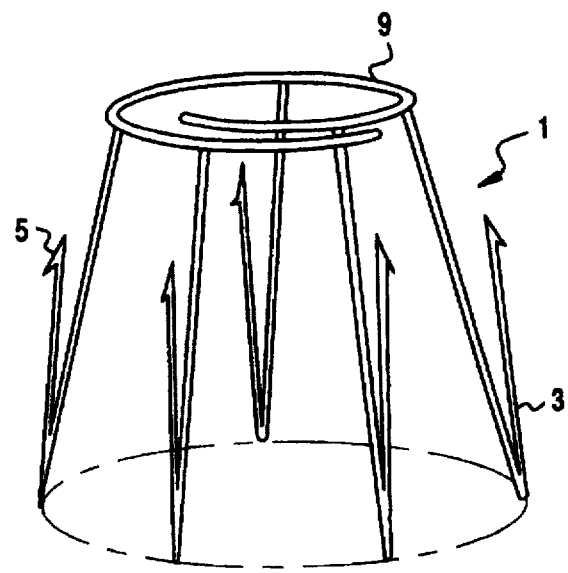

FIG. 3 shows another permanent filter such as may be included in the filtration unit according to the invention. Here, the various "V"-shaped branches 3 are connected by one of their free ends to a metal head structure 9 having an axial spirally wounded configuration to form a "watch spring" type structure of which the central opening has an "elastic" diameter which can likewise be reduced or expanded. Like the filter of FIG. 2, this filter can adopt a constrained or spread state. It can likewise be formed either in several pieces or in one single piece.

The various stages of introducing the blood filtration unit according to the invention into a vessel will now be described with reference to FIGS. 4 to 10.

Figure 4:
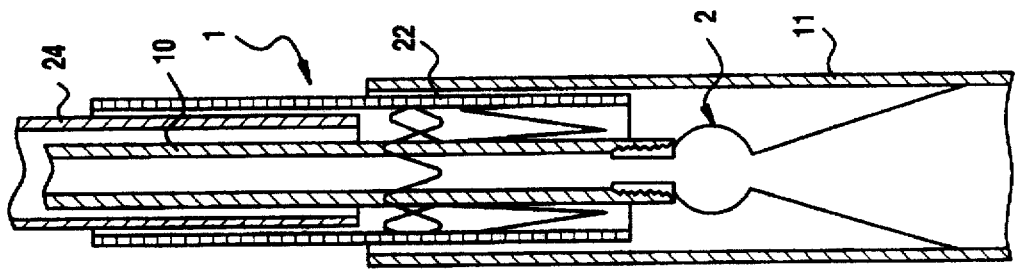

FIG. 4 shows diagrammatically the introduction of the temporary filter, which is to be implanted first. The temporary filter 2 is in the radially folded state in a first catheter 20 and the assembly is slid into the vessel 11 along a guide wire 14 until it reaches the place of implantation.

Figure 5:
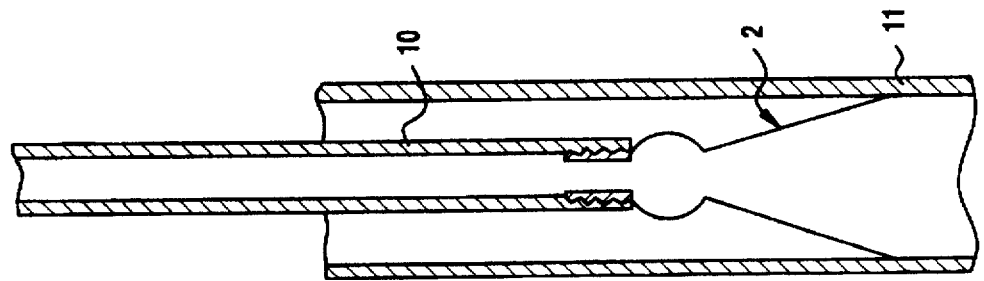

In order to position the filter in the vessel, it is then necessary, as shown in FIG. 5, only to displace the catheter 20 and the filter 2 in relative translation so that the legs 3 of the latter spread out and rest on the wall of the vessel 11.

Figure 6:
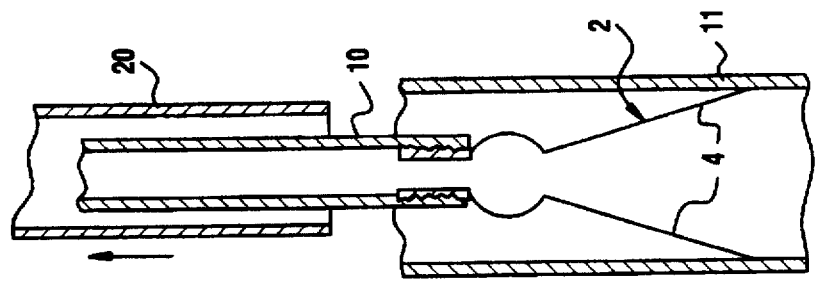

FIG. 6 shows the filter 2 in its spread position in the vessel 11.

Figure 7:
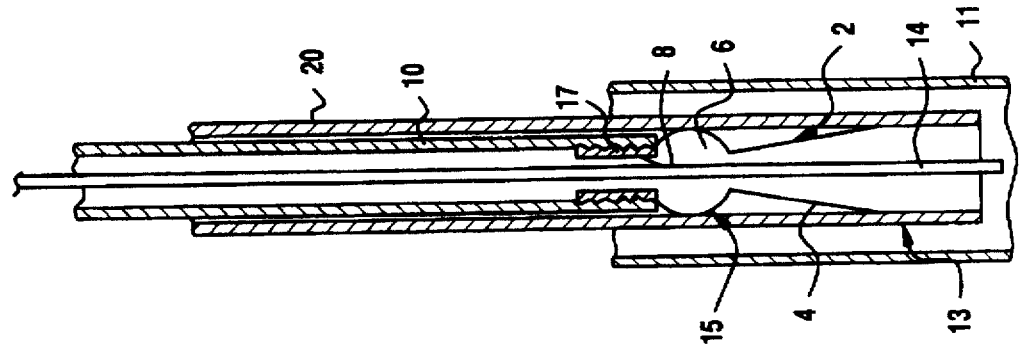

FIG. 7 shows how the permanent filter 1 is introduced. The latter is in the constrained state in a second catheter 22 in which a third catheter 24 is also inserted. The assembly is slid into the vessel 11 until it reaches the place where the temporary filter 2 is implanted.

FIG. 8 shows diagrammatically the removal of the temporary filter 2. When the surgeon pulls the flexible support tube 10 in the direction of arrow 14, the temporary filter 2 penetrates into the catheter 22, then passes through the permanent filter 1 while, if necessary, widening the diameter of the central opening of the latter as it passes through. The temporary filter 2 then slides into the catheter 24, before being withdrawn entirely from the vessel. After the passage of the temporary filter 2, the diameter of the central opening of the permanent filter goes back to its restrained diameter. It could, however, also remain radially widened.

The permanent filter is then introduced into the vessel by displacing the catheter 22 in the direction of arrow 16 in relative transition with respect to the catheter 24. The legs 3 spread out and attach themselves to the wall of the vessel 11 by means of the hooks 5.

The blood filtration unit according to the invention therefore permits the use of temporary filters which may be less bulky and therefore less troublesome to the patient than those described in the prior art and, on the other hand, the use of more bulky permanent filters which therefore have a filtering capacity which is much greater than those used hitherto in this type of unit.

In addition, because the permanent filter can be traversed by a central opening of variable diameter, it is possible to withdraw any conventional type of temporary filter through it, the size of the opening adapting itself to the size of each temporary filter. This is very advantageous from the practical point of view and permits great flexibility in the choice of temporary filter used.

The same results could also be obtained by implanting the permanent filter before removing the temporary filter. It would then be possible to use a permanent filter 1 having a central opening of which the diameter widens during the expansion of the filter and remains in that position in order to allow the temporary filter 2 to pass through.

The permanent filter 1 could also be a filter of which the diameter remains constricted during implantation and widens under the action of the temporary filter 2 as the latter passes through.

Equally, in another variant, it would be possible to employ a catheter 20 which is used both for the introduction of the two filters and the removal of the temporary filter, thus dispensing with the catheter 24.

I claim:

1. A blood filtration unit adapted to be implanted within a vessel of a patient body, especially for retaining blood clots therein, the blood filtration unit comprising:

a first blood filter adapted to be temporarily implanted in the vessel, during a first period of time, said first blood filter comprising:

a filtration structure having an axis and being adapted for having a first reduced diameter in a first radially folded state, for the implantation thereof, and a second enlarged diameter greater than the first diameter, in a radially expanded state, upon implantation of said filtration structure in the vessel, an elongated flexible support-stem having an end fixed to said filtration structure, the elongated support stem having a length enough for controlling a movement of the filtration structure, from outside the patient body, a first catheter adapted to be introduced into the vessel and adapted for containing the first blood filter in its first radially folded state, for the implantation thereof in the vessel a second blood filter adapted to be permanently implanted in the vessel, during a second period of time following the first period of time, the second blood filter having a central hole for allowing the passage therethrough of the first blood filter in its first radially folded state, the second blood filter being adapted for having a first reduced diameter in a first radially folded state, for the implantation thereof in the vessel, and a second enlarged diameter greater than the first diameter, in a second radially expanded state, upon implantation of said second blood filter in the vessel, a second catheter adapted to be introduced in the vessel and adapted for containing the second blood filter in its first radially folded state, for the implantation thereof in the vessel, and/or for containing the first blood filter in its first radially folded state for removing thereof out of the vessel, at the end of said first period of time.

2. The filtration unit according to claim 1, wherein the central hole of the second blood filter has a variable diameter adapted to be reduced or expanded.

3. The filtration unit according to claim 1, wherein the second blood filter has an axis and comprises elongated legs extended substantially parallel to said axis in the first radially folded state, said legs comprising fixation means for fixing said second blood filter to the vessel, and a head structure having ondulations defining an axial ring connected to the elongated legs at one end thereof, said legs comprising fixation means for fixing said second blood filter to the vessel.

4. The filtration unit according to claim 1, wherein the second blood filter has an axis and comprises elongated legs extending substantially parallel to said axis in the first radially folded state, and a head structure having an axial spirally wounded configuration and connected to the elongated legs at one end thereof, said legs comprising fixation means for fixing said second blood filter to the vessel.

5. The filtration unit according to claim 1, further comprising a third catheter adapted to be introduced into the second catheter, so that to allow an axial movement of the second blood filter relative to the second catheter, for implanting the second blood filter in the vessel.

6. The filtration unit according to claim 5, wherein the third catheter is adapted for containing the first blood filter in the first radially folded state thereof, for removing said first blood filter out of the vessel.

7. The filtration unit according to claim 1, wherein the elongated support-stem is a flexible tube.

* * * * *